US009513239B2

(12) United States Patent
Yang et al.

(10) Patent No.: US 9,513,239 B2
(45) Date of Patent: Dec. 6, 2016

(54) TOOL CASING DETECTION (71) Applicant: Halliburton Energy Services, Inc., Houston, TX (US)

(72) Inventors: Jie Yang, Paoli, PA (US); Rebecca Corina Jachmann, Spring, TX (US); Songhua Chen, Katy, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/387,485

(22) PCT Filed: Jul. 29, 2013

(86) PCT No.: PCT/US2013/052535
§ 371 (c)(1),
(2) Date: Sep. 23, 2014

(87) PCT Pub. No.: WO2015/016811
PCT Pub. Date: Feb. 5, 2015

(65) Prior Publication Data
US 2016/0245763 A1    Aug. 25, 2016

(51) Int. Cl.
*G01V 3/00* (2006.01)
*G01N 24/08* (2006.01)
*G01V 3/32* (2006.01)
*G01V 3/38* (2006.01)
*G01R 33/54* (2006.01)
*E21B 47/09* (2012.01)

(52) U.S. Cl.
CPC ............. *G01N 24/081* (2013.01); *E21B 47/09* (2013.01); *G01R 33/543* (2013.01); *G01V 3/32* (2013.01); *G01V 3/38* (2013.01)

(58) Field of Classification Search
CPC .................................................... G01R 33/543
USPC ........................................ 324/303, 314, 300
See application file for complete search history.

(56) References Cited

U.S. PATENT DOCUMENTS

| 6,717,404 B2 | 4/2004 | Prammer |
| 6,808,028 B2 | 10/2004 | Woodburn et al. |
| 7,363,967 B2* | 4/2008 | Burris, II ............... E21B 23/00 166/254.1 |
| 7,937,223 B2 | 5/2011 | Ciglenec et al. |
| 7,960,969 B2 | 6/2011 | Mouget et al. |
| 8,165,825 B2 | 4/2012 | Legendre |

(Continued)

OTHER PUBLICATIONS

Mitchell, J., et al., "A rapid measurement of T1/T2T1/T2: The DECPMG sequence", *Journal of Magnetic Resonance*, 200(2), (Oct. 2009), 198-206.

(Continued)

*Primary Examiner* — Louis Arana
(74) *Attorney, Agent, or Firm* — Schwegman Lundberg & Woessner, P.A.; Benjamin Fite (57) ABSTRACT Various embodiments include apparatus and methods to conduct testing related to the disposition of measuring tools downhole in a borehole, where the measuring tools are deployed to perform testing to evaluate properties of regions in the borehole. A plurality of test analyses on data collected from operating a measuring device of a measuring tool in the borehole can be used to determine whether the measuring device is in casing or out of casing. Additional apparatus, systems, and methods are disclosed.

29 Claims, 6 Drawing Sheets

(56) References Cited

U.S. PATENT DOCUMENTS

| | | |
|---|---|---|
| 2004/0200083 A1 | 10/2004 | Yarbro |
| 2009/0095469 A1 | 4/2009 | Dozier |
| 2010/0132449 A1 | 6/2010 | Birkett et al. |
| 2011/0285398 A1 | 11/2011 | Villegas et al. |
| 2012/0226443 A1* | 9/2012 | Cresswell ............... E21B 47/04 |
| | | 702/11 |
| 2013/0056202 A1* | 3/2013 | Maida ................... E21B 47/123 |
| | | 166/255.1 |

OTHER PUBLICATIONS

Prammer, M. G, et al., "A New Multiband Generation of NMR Logging Tools", *SPE Reservoir Evaluation & Engineering*, 4(1), (Feb. 2001), 59-63.

"International Application Serial No. PCT/US2013/052535, International Search Report mailed Apr. 22, 2014", 3 pgs.

"International Application Serial No. PCT/US2013/052535, Written Opinion mailed Apr. 22, 2014", 6 pgs.

\* cited by examiner

TOOL CASING DETECTION

PRIORITY APPLICATION

This application is a U.S. National Stage Filing under 35 U.S.C. 371 from International Application No. PCT/US2013/052535, Filed on 29 Jul 2013; which application is incorporated herein by reference in its entirety.

TECHNICAL FIELD

The present invention relates generally to apparatus for making and evaluating measurements.

BACKGROUND

In drilling wells for oil and gas exploration, understanding the structure and properties of the associated geological formation provides information to aid such exploration. Measurements in a borehole are typically performed to attain this understanding. Measurements can be made by tools conveyed into the regions of interest within a casing, but with tools activated when not in the casing. It is important to be able to determine whether tools are in casing. This determination may be especially significant for nuclear magnetic resonance tools. Firing in casing not only wastes energy, but can also short a tool's antenna or other components, or other measuring device, and potentially damage the hardware. Firing in casing can also produce false logs. For example, if casing is not detected when a tool is in a large diameter riser pipe section, the tool may not be overstressed in operation, but may produce a false log. Therefore, casing detection can be valuable for logging tools. In some standard approaches, only resonant frequency calculated by the gain amplitude maximum would be used to detect casing. The usefulness of such measurements may be related to the precision or quality of the process of making measurements for casing detection.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, the system gain response can be used to detect whether a tool is in casing. The in casing condition may include housing of the tool or other structure to which the tool is mounted, such as, but not limited to a drill collar or drill pipe. NMR sensor system gain is proportional to the resonance circuit quality factor Q of the NMR receiver antenna. The antenna Q is affected by the damping effects caused by the environment, which includes the conductivity of the borehole and formation fluids, and, for the same reason, a conductive metal pipe affects the Q value and the gain. An antenna has intrinsic inductance and resistance. When an antenna is in a metal pipe, its apparent inductance reduces. Since Q is defined as $\omega L/R$, a reduction in L results in the reduction of Q. As the result, the system gain response with an antenna or measuring device of the tool in casing is different from the system gain response with the antenna or measuring device of the tool not being in casing. In addition, the resonant frequency, $$\omega = \frac{1}{\sqrt{LC}},$$

goes up with the antenna or measuring device of the tool in casing relative to the antenna or measuring device of the tool not being in casing. Gain (G) and inductance (L) are related by:

$$G = I$$
$$= \frac{v}{z}$$
$$= (A\sin\omega t)\left(\frac{1}{j\omega L + R_1} + \frac{1}{R_L} + j\omega C\right),$$

where v is voltage, z is impedance, $R_1$ is antenna resistance, $R_L$ is load resistance, C is antenna capacitor, A is amplitude, and $\omega$ is frequency.

In various embodiments, use of a combination of analyses can add dimensions of evaluation compared to a standard gain check. A complex gain can be measured with real and imaginary components. When a measuring device, such as an antenna, is changed from one environment to another, electrical parameters can change in a predictable manner. When casing is introduced into the antenna's environment, its presence is reflected as a change in equivalent electrical parameters, producing a significant change in electrical resonance frequency and the complex gain values during a measurement. A process can be implemented to detect the presence of casing by measuring the device's impedance, such as antenna impedance, because of the changes in antenna induction. A process can utilize a gain frequency sweep curve to detect casing.

A casing detection process can include a number of tests as a function of frequency, where the tests can include gain amplitude, phase, imaginary part of the gain, and Q, where Q is a quality factor. The gain amplitude can be given by $$|G|=\sqrt{(G_{imag})^2+(G_{real})^2},$$

where $G_{imag}$ and $G_{real}$ are the imaginary part and real part, respectively, of the gain. The quality factor, Q, can be given by $$Q \rightarrow Q = \frac{f_0}{f_0^+ - f_0^-},$$

where $f_0^+$ is a frequency (upper frequency) greater than a resonant frequency, $f_0$, at which the amplitude of the gain is at a selected percentage of the amplitude at $f_0$, and $f_0^-$ is a frequency (lower frequency) below $f_0$ at which the amplitude of the gain is also at the selected percentage of the amplitude at $f_0$. The selected percentage of the amplitude can range from 50% to 95%. The quality factor can be set relative to other percentages such as, but not limited to, 50%. The difference $f_0^+-f_0^-$ is an effective bandwidth. The gain phase, θ, can be given by $$\theta=\arctan(G_{imag}/G_{real}).$$

Imaginary zero crossing can be used to provide information to determine the presence of casing, in addition to gain amplitude, Q, and gain phase.

In a low Q environment, the amplitude measurement can be noisy. Further, a non-linear curve fit for gain amplitude may not be as appropriate as linear fit of phase or imaginary for data near zero crossing. By combining gain amplitude, phase, imaginary part, and Q, a determination, as to whether a measuring device of a tool is in casing, may be made with enhanced confidence. The combination of test analyses can be performed as a function of frequency. In addition, the combination of test analyses may use a common set of data. Each test analysis of the combination of test analyses can be structured based on the gain response of the measuring device.

In various embodiments, analysis of a set of tests can be conducted such that if a test is indeterminate regarding the position of a measuring device with respect to being in casing, another test of the set can be analyzed until a definitive result is obtained. If there are remaining test(s) in the set to be analyzed, these remaining tests can be conducted for verification. In addition, for a given application, the absence of a signal can be used to trigger making measurements for the set of tests. The set of tests can include any number of the tests, which can be conducted in any order. The set of tests can include a center frequency test of the measuring device, a zero crossing test, and a Q test. The measuring device of the tool may be an antenna.

Figure 1:
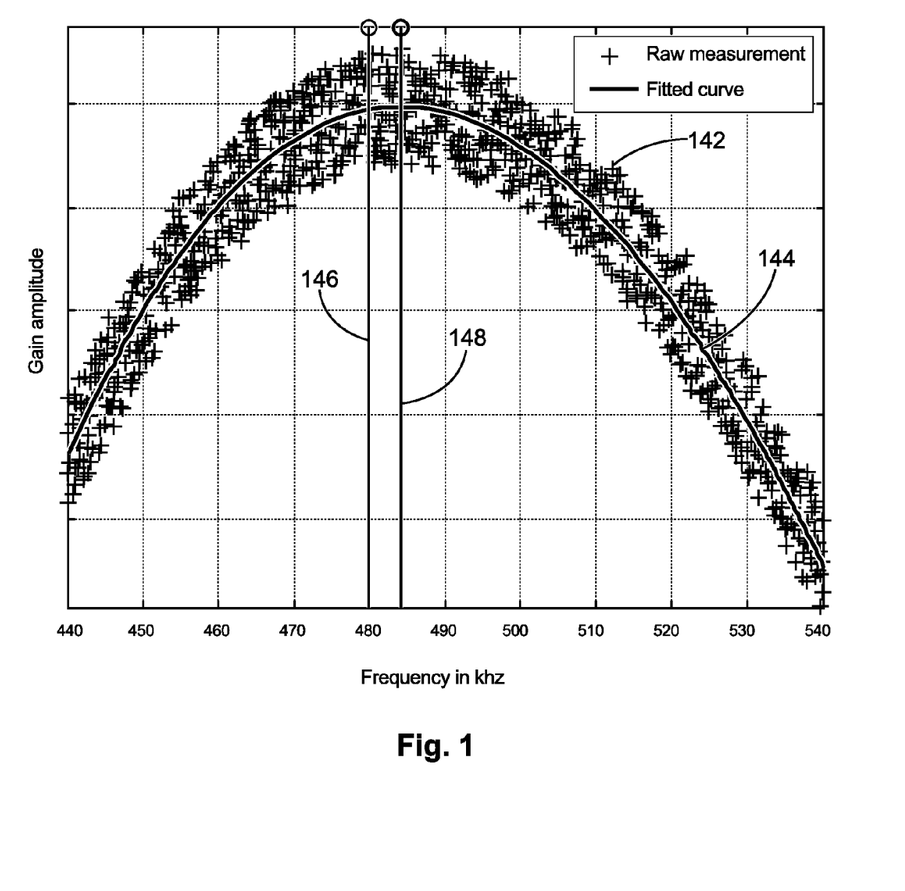
FIG. 1 shows gain amplitude as a function or frequency for an antenna having selected characteristic values, in accordance with various embodiments.
Figure 2:
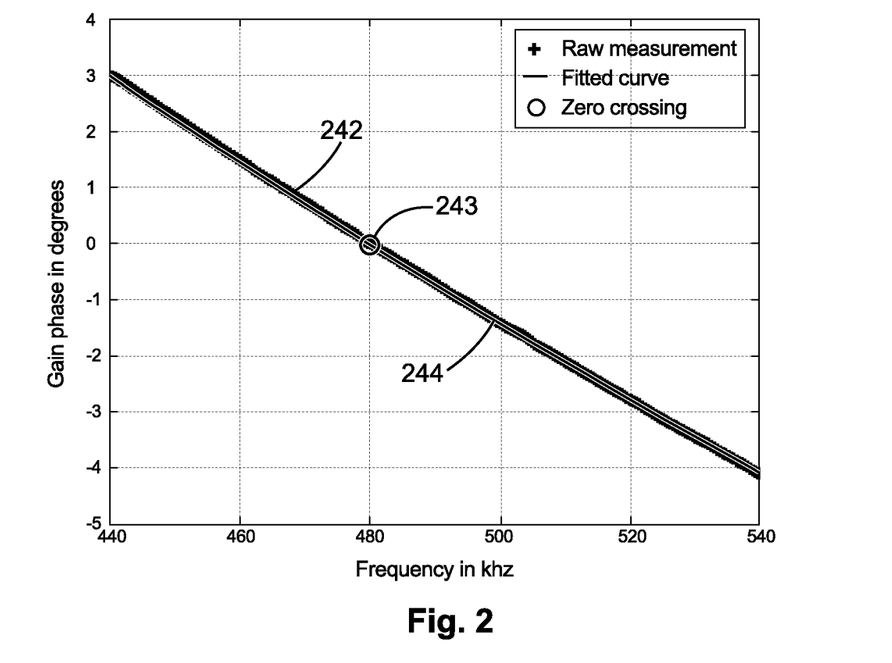
FIG. 2 shows the phase of the gain of the antenna of FIG. 1 having the selected characteristic values, in accordance with various embodiments.
Figure 3:
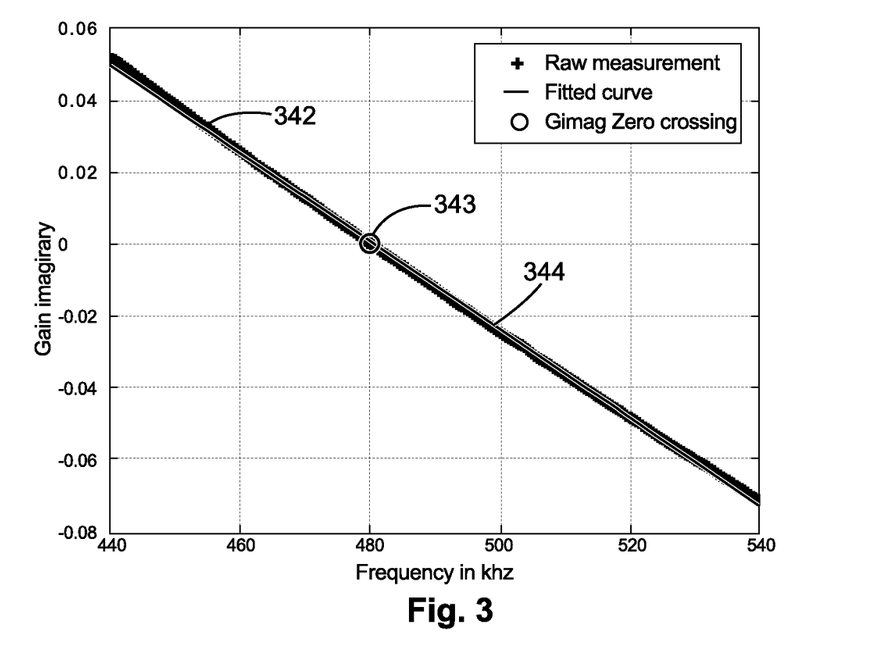
FIG. 3 the imaginary component of the gain of FIG. 1 having the selected characteristic values as a function of frequency, in accordance with various embodiments.

FIGS. 1-3 show an example of test data on an antenna for a selected set of characteristics ($R_1$, L, C, $R_L$). FIG. 1 shows gain amplitude as a function of frequency for the antenna having these selected characteristics. Raw measurements 142 and a fitted curve 144 are shown with a measured resonant frequency of the antenna of 484.105 kHz shown by line 148, where the real resonant frequency of the antenna is 479.870 kHz shown by line 146. When the tool is in casing, the apparent inductance is reduced and Q is decreased.

FIG. 2 shows the phase of the gain for the antenna of FIG. 1 having the selected characteristics. The phase of the gain can be calculated for the antenna, other measuring device over a range of frequencies, which can be represented with respect to a resultant Q value. The frequency at which this phase is zero is known as the "phase zero crossing" or "zero phase crossing." Shown in FIG. 2 are phase zero crossing 243 in the raw measurements 242 and fitted curve 244. The frequency at phase zero crossing 243 is also the antenna's resonant frequency. This number is less sensitive to noise and is a good test of whether a tool is in casing. An alternative embodiment to phase zero crossing can be implemented directly using the zero-crossing of the imaginary component of the gain, $G_{imag}$.

FIG. 3 shows the imaginary component of the gain for the antenna of FIG. 1 having the selected characteristics. The imaginary component is shown as a function of frequency for the antenna over a range of frequencies, which can be represented with respect to a resultant Q value. Shown in FIG. 3 are the raw measurements 342 and fitted curve 344. The frequency at which this imaginary component of the gain is zero, shown at 343, is also the antenna's resonant frequency.

Figure 4:
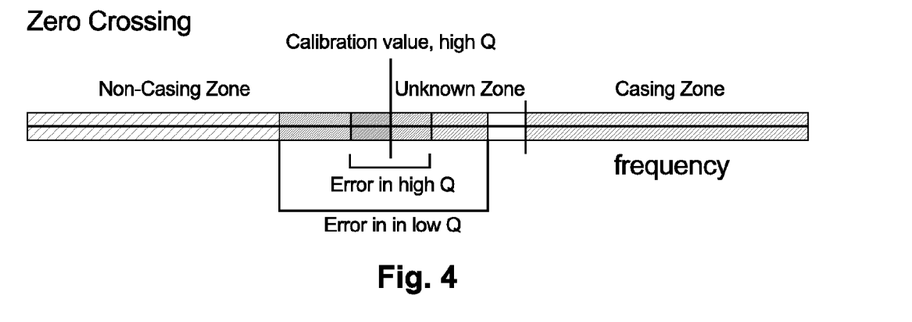
FIGS. 4-6 show parameters regarding measured data compared with calibration data, in accordance with various embodiments.
Figure 5:
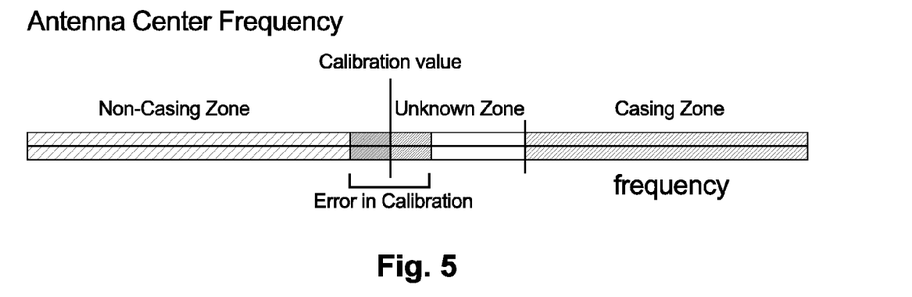
Figure 6:
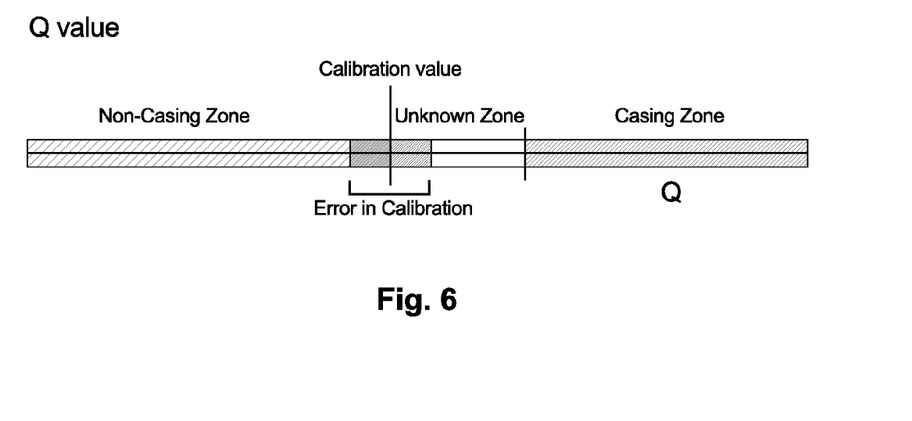

For each test, a standard value can be used in the analysis. Each standard value can be found through calibration under a high Q environment, which is known to be a safe, casing free. Each of the values for each test can be designated, as shown in FIGS. 4-6, as a "calibration value." Each value can have an error associated with it. Within that error it is not possible to determine if a tool is in casing or outside casing. FIGS. 4-6 show parameters regarding measured data compared with calibration data. These parameters can form a basis of a process to determine whether the measurement device of a tool may be in casing or not.

During calibration processes, resonant frequency, phase zero-crossing frequency, and Q can be measured as reference points. When tools are logging, the resonant frequency, the phase zero-crossing frequency and the Q are measured. By comparing the value differences between logging data and calibration data, presence of casing can be detected. But due to uncertainty with the measured resonant frequency, the phase zero-crossing frequency, and the Q in logging and calibration, there are unknown zones associated with each measurement, as shown in FIGS. 4-6. By combining information from all possible tests, casing can be detected with enhanced confidence.

When a quantity is measured in a test, and if the result is in the known zone according to its calibration, which can be either out of casing or in casing, then no further test needs to be performed. If the test value is in the unknown range, then the next test can be conducted until one of the tests can conclude, as a result, with the occurrence of casing or non-casing as a determinate status. If a determination is made in a test, the remaining test(s) can be performed for verification. It is noted that conducting a given test can include analysis of a set of data for the given test.

For a given application, the absence of a signal can be used to trigger a process to make measurements for conducting the set of tests. For example, when the measured porosity drops to zero or to within a selected range greater than zero, there is a chance that the tool has gone into casing since no signal comes from casing. The selected range may be set based on similar measurements and data taken or other analysis results stored in a database. This condition can be a trigger to check for casing. If casing is not found, a loop can be set up where a signal check is part of the casing detection process. This loop can include checking for casing, where if none of the plurality of tests gives a positive reading for casing, a signal check can be conducted. If a signal comes back in response to the signal check, then it can be safely assumed that the tool is not in casing.

An embodiment for combining three parameters can include a process to compute $$\left| \Delta f_{z-c} \cdot \Delta f_{ga} \cdot \frac{Q_{CAL}}{Q} \right| > \text{pre-determined value or}$$

$$\left| \Delta f_{z-c} \cdot \Delta f_{ga} \cdot \frac{\Delta f}{\Delta f_{cal}} \right| > \text{pre-}determined \text{ value.}$$

where $\Delta f_{z-c}$ is the frequency shift corresponding to zero-crossing, $\Delta f_{ga}$ is the frequency shift corresponding to maximum gain amplitude frequency shift between the calibrated value and the measured value, and $$\frac{\Delta f}{\Delta f_{cal}}$$

is the resonant circuit bandwidth ratio between the measured value and the calibrated value. Similarly, $$\frac{Q_{CAL}}{Q}$$

is a resonant ratio for the quality factor. With the condition of the selected comparison satisfied, the status of the measuring status can be taken to be in casing.

Phase zero-crossing curve fit, imaginary part zero crossing, and Q information as taught herein provides additional processes to determine whether a measuring device is inside or outside casing. These processes can provide greater confidence in the results than conventional measurements that only use resonant frequency measured with gain amplitude. In addition, since phase and imaginary part curves near zero-crossing are quasi-linear, zero-crossing detection is computationally less intensive and more stable compared to amplitude curve fitting, which is non-linear. Applying processes, as taught herein, may provide casing detection that is more accurate. By reducing the probability of false casing detection, log data density may be improved. As the result, hardware may be better protected and power may be better saved. For example, when a battery is used, cost can be reduced significantly from casing detection using the combined testing approach.

Figure 7:
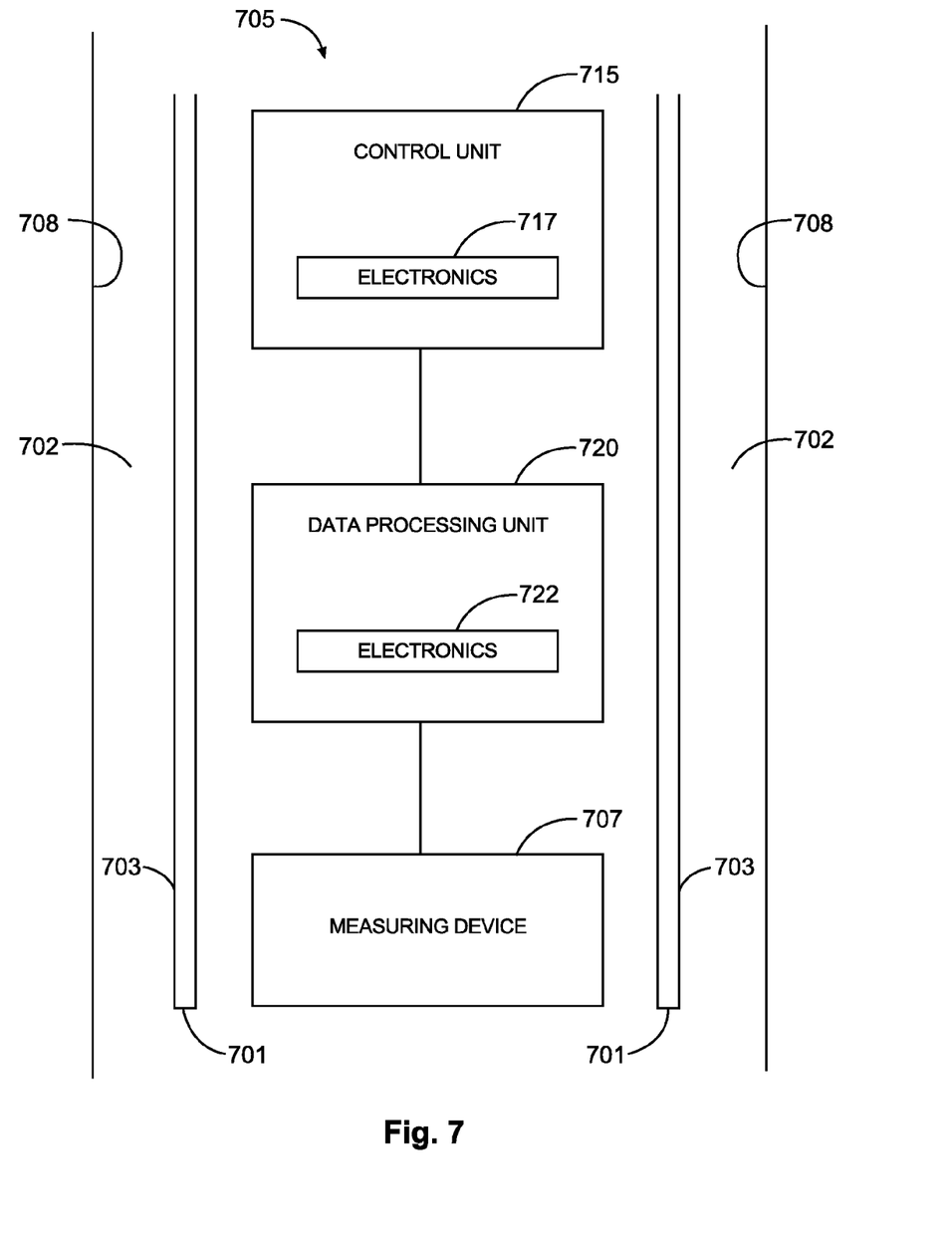
FIG. 7 shows a block diagram of an example tool disposed in a borehole, operable to conduct downhole testing, in accordance with various embodiments.

FIG. 7 shows a block diagram of an example embodiment of a tool 705 disposed in borehole 702 operable to conduct downhole testing. The borehole 702 is defined by walls 708. The tool 705 can include a measuring device 707, a control unit 715, and a data processing unit 720. The control unit 715 and the data processing unit 720 include electronics 717 and 722, respectively, to evaluate whether the measuring device 707 is in casing 703 or the measuring device 707 is out of casing 703. The casing 703 has an end 701, beyond which the measuring device 707 can extend. There may be cement, other casing, or other material between the casing 703 and the walls 708 of the borehole 702.

The electronics 722 of the data processing unit 720 can be constructed to conduct a plurality of test analyses on data collected from operating the measuring device 707, where the plurality of test analyses are structured to determine whether the measuring device 707 is in casing or out of casing. The plurality of test analyses can include combinations of the test procedures discussed herein. For example, the plurality of test analyses can include conducting three test analyzes in a sequential order, where if one of the test analysis is determinate of the in/out position of the measuring device 707, the remaining test analyses are conducted as a verification procedure. The sequential order of the plurality of test analyses may be in any selected order. The collected data can include responses received by the measuring device 707 in response to the measuring device 707 operating to generate signals to probe an underground formation. The combination of test analyses can be performed as a function of frequency. In addition, the combination of test analyses may use a common set of data. Each test analysis of the combination of test analyses can be structured based on the gain response of the measuring device 707.

The electronics 717 of the control unit 715 can be constructed to control the measuring device 707 based on results of the test analyses. The control can include continuing the probing of the underground formation, halting the probing of the underground formation, moving the measuring device 707 such that the measuring device 707 is out of casing to probe downhole, or other activity to protect the measuring device 707 or enhance the accuracy of the testing of the properties of regions downhole.

The control unit 715, the data processing unit 720, or combinations of the control unit 715 and the data processing unit 720 can be arranged to control operation of the measuring device 707 to generate the signals to probe the underground formation. To provide data for the test analyses to determine the in/out position of the measuring device 707, the generation of signals can include generating signals over a range of frequencies. The range of frequencies can include the resonant frequency of the measuring device 707. In addition, the control unit 715, the data processing unit 720, or combinations of the control unit 715 and the data processing unit 720 can be arranged to control operation of the measuring device 707 to collect signals in response to the probing of the underground formation. The control unit 715 and the data processing unit 720 may be separate units or the control unit 715 and the data processing unit 720 may be an integrated unit. The data processing unit 720, the control unit 415, or the combination of the data processing unit 720 and the control unit 415, either individually or together, can be integrated with the measuring device 707 or structured as distributed components. Distributed components can include components at the surface at a drilling location or downhole. In addition, the tool 705 can be structured for operation in a wireline system or in a measure-while-drilling (MWD) system such as a logging-while-drilling (LWD) system.

In various embodiments, a system including the tool 705 can be arranged to operate the control unit 715, the data processing unit 720, or both the control unit 715 and the data processing unit 720 in a variety of ways. The data processing unit 720 can be operable to conduct the plurality of test analyses in a sequential fashion. The data processing unit 720 can be operable to conduct one or more test analyses of the plurality of test analyses, after the result of one test analysis of the plurality of test analyses is determinate as to whether the measuring device 707 is in casing or out of casing, to provide a verification procedure. The plurality of test analyses can be structured to include conducting a center frequency test of the measuring device 707, a zero crossing test of the measuring device, and a Q test of the measuring device. The zero crossing test can be a determination of zero crossing of phase of a measured gain as a function of frequency. The zero crossing test can be a determination of zero crossing of an imaginary part of a measured gain as a function of frequency. The data processing unit 720 can be operable to determine the measuring device 707 to be out of casing from the result of a test analysis of the plurality of test analyses having a measurement test quantity being lower than a calibration value of the test analysis by more than an associated error. The data processing unit 720 can be operable to determine the measuring device 707 to be in casing from the result of a test analysis of the plurality of test analyses having a measurement test quantity being greater than a calibration value of the test analysis by more than a known value. The known value can be greater than the calibration value of the test analysis by more than an associated error. The data processing unit 720 can be operable to conduct the plurality of test analyses to include a comparison of a pre-determined value to absolute value of a product of a frequency shift corresponding to a zero-crossing, a frequency shift corresponding to maximum gain amplitude frequency shift, and a resonant ratio for a quality factor. The data processing unit 720 can be operable to conduct the plurality of test analyses to include a comparison of a pre-determined value to absolute value of a product of a frequency shift corresponding to a zero-crossing, a frequency shift corresponding to maximum gain amplitude frequency shift, and a ratio between a calibrated value of a resonant circuit bandwidth and a measured value of a resonant circuit bandwidth.

The control unit 715 and the data processing unit 720 can be operable together to conduct the plurality of test analyses following a trigger generated in response to an occurrence of an operational measuring event. The occurrence of the operational measuring event can include detection of an absence of a measurement value in an analysis system or detection of an absence of reception of a measurement signal. The occurrence of the operational measuring event can include detection that porosity of a formation being measured drops to close to zero.

Figure 8:
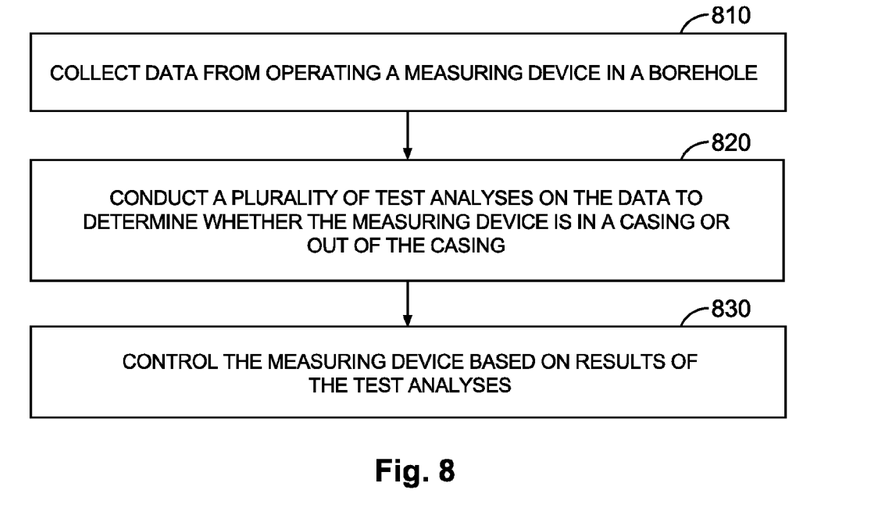
FIG. 8 shows features of an example method to operate a measurement tool downhole, in accordance with various embodiments.

FIG. 8 shows features of an embodiment of a method to operate a measurement tool downhole. At 810, data is collected from operating a measuring device in a borehole. The data may be collected directly from receivers of the measuring device relative to signals generated form the measuring device. Measurement signals at the measuring device can be collected downhole and transmitted to a data processing unit that is at the surface of the well.

At 820, a plurality of test analyses is conducted on the data to determine whether the measuring device is in casing or out of casing. The plurality of test analyses can be performed as a function of frequency. In addition, the plurality of test analyses may use a common set of data. Each test analysis of plurality of test analyses can be structured based on the gain response of the measuring device. Conducting the plurality of test analyses can include conducting the plurality of test analyses in a sequential fashion. Conducting one or more test analyses of the plurality of test analyses, after the result of one test analysis of the plurality of test analyses is determinate as to whether the measuring device is in casing or out of casing, can be conducted as a verification procedure. Conducting the plurality of test analyses can include conducting a center frequency test of the measuring device, a zero crossing test of the measuring device, and a Q test of the measuring device. The zero crossing test can be a determination of zero crossing of phase of a measured gain as a function of frequency. The zero crossing test can be a determination of zero crossing of an imaginary part of a measured gain as a function of frequency.

Determining the measuring device to be out of casing can include the result of a test analysis of the plurality of test analyses having a measurement test quantity being lower than a calibration value of the test analysis by more than an associated error. Determining the measuring device to be in casing can include the result of a test analysis of the plurality of test analyses having a measurement test quantity being greater than a calibration value of the test analysis by more than a known value. The known value can be a value greater than the calibration value of the test analysis by more than an associated error. Performing determinations based on measured values being less than or greater calibration values of the various tests takes into consideration that there can be zones in the range of measurements that are effectively unknown zones as to whether the measured values of the tests are determinate of the in/out status of the measuring device.

Conducting the plurality of test analyses can include comparing a pre-determined value to an absolute value of a product of a frequency shift corresponding to a zero-crossing, a frequency shift corresponding to maximum gain amplitude frequency shift, and a resonant ratio for a quality factor. Conducting the plurality of test analyses can include comparing a pre-determined value to absolute value of a product of a frequency shift corresponding to a zero-crossing, a frequency shift corresponding to maximum gain amplitude frequency shift, and a ratio between a calibrated value of a resonant circuit bandwidth and a measured value of a resonant circuit bandwidth.

Conducting the plurality of test analyses on the data can be triggered by an occurrence of an operational measuring event. The occurrence of the operational measuring event can include detection of an absence of a measurement value in an analysis system or detection of an absence of reception of a measurement signal. The occurrence of the operational measuring event can include detection that porosity of a formation being measured drops to close to zero.

At 830, the measuring device is controlled based on results of the test analyses. Based on the results of the plurality of test analyses, the measuring device can be controlled to continue probing in the borehole. Based on the results of the plurality of test analyses, the measuring device can be controlled to halt the probing in the borehole. Controlling the measuring device based on results of the test analyses can include moving the measuring device such that the measuring device is out of casing to probe in the borehole. Controlling the measuring device based on results of the test analyses can include performing other activities to protect the measuring device or enhance the accuracy of the testing of the properties of regions downhole.

Implementations can include a machine-readable storage device having machine-executable instructions, such as a computer-readable storage device having computer-executable instructions, when performed by a machine, cause the machine to perform operations, the operations comprising actions to: collect data from operating a measuring device in a borehole; conduct a plurality of test analyses on the data to determine whether the measuring device is in casing or out of casing, each test analysis of the plurality of test analyses being based on a function of frequency; and control the measuring device based on results of the test analyses. In addition, the plurality of test analyses may use a common set of data. Each test analysis of the plurality of test analyses can be structured based on the gain response of the measuring device. The instructions can be executed by one or more processors operating on instructions in one or more machine-readable storage devices.

Instructions to conduct the plurality of test analyses can include one or more instructions to conduct the plurality of test analyses in a sequential fashion. Instructions can include one or more instructions to conduct one or more test analyses of the plurality of test analyses, after the result of one test analysis of the plurality of test analyses is determinate as to whether the measuring device is in casing or out of casing, as a verification procedure. Instructions to conduct the plurality of test analyses can include one or more instructions to conduct a center frequency test of the measuring device, a zero crossing test of the measuring device, and a Q test of the measuring device. The zero crossing test can be a determination of zero crossing of phase of a measured gain as a function of frequency. The zero crossing test can be a determination of zero crossing of an imaginary part of a measured gain as a function of frequency.

Instructions to determine the measuring device to be out of casing can include one or more instructions to use the result of a test analysis of the plurality of test analyses having a measurement test quantity being lower than a calibration value of the test analysis by more than an associated error. Instructions to determine the measuring device to be in casing can include one or more instructions to use the result of a test analysis of the plurality of test analyses having a measurement test quantity being greater than a calibration value of the test analysis by more than a known value. The known value can be selected as a value providing enough confidence with respect to the calibration value. The known value may be selected based on a statistical confidence level. The known value can be greater than the calibration value of the test analysis by more than an associated error. Instructions to conduct the plurality of test analyses can include one or more instructions to compare a pre-determined value to an absolute value of a product of a frequency shift corresponding to a zero-crossing, a frequency shift corresponding to maximum gain amplitude frequency shift, and a resonant ratio for a quality factor. Instructions to conduct the plurality of test analyses can include one of more instructions to compare a pre-determined value to absolute value of a product of a frequency shift corresponding to a zero-crossing, a frequency shift corresponding to maximum gain amplitude frequency shift, and a ratio between a calibrated value of a resonant circuit bandwidth and a measured value of a resonant circuit bandwidth.

Instructions can also include instructions to conduct the plurality of test analyses triggered by an occurrence of an operational measuring event. The occurrence of the operational measuring event can include detection of an absence of a measurement value in an analysis system or detection of an absence measurement tool of reception of a measurement signal. The occurrence of the operational measuring event can include detection that porosity of a formation being measured drops to close to zero.

Instructions can include instructions to operate a tool to provide data to a data processing unit such that the data processing unit conducts one or more processes in accordance with the teachings herein. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

Figure 9:
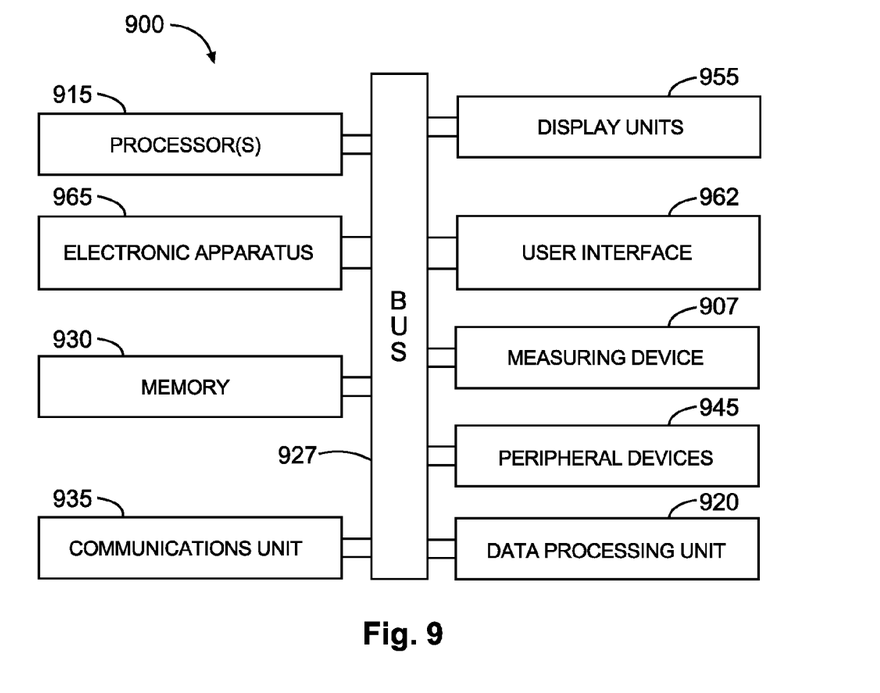
FIG. 9 depicts a block diagram of features of an example system operable to evaluate whether a measuring device operable in a borehole is in casing or the measuring device is out of casing, in accordance with various embodiments.

FIG. 9 depicts a block diagram of features of an example embodiment of a system 900 operable to evaluate whether a measuring device 907 operable in a borehole is in casing or the measuring device 907 is out of casing. The system can be constructed to conduct a plurality of test analyses on data collected operating the measuring device 907, where the plurality of test analyses are structured to determine whether the measuring device 907 is in casing or out of casing. The plurality of test analyses can include combinations of test procedures similar to or identical to test analyses discussed herein. For example, the plurality of test analyses can include conducting three test analyzes in a sequential order, where if one of the test analysis is determinate of the in/out position of the measuring device 907, the remaining test analyses are conducted as a verification procedure. The sequential order of the plurality of test analyses may be in any selected order. The collected data can include responses received by the measuring device 907 in response to the measuring device 907 operating to generate signals to probe an underground formation. The combination of test analyses can be performed as a function of frequency. In addition, the combination of test analyses may use a common set of data. Each test analysis of the combination of test analyses can be structured based on the gain response of the measuring device 907. The system 900 can be configured to operate in accordance with the processes and procedures taught teachings herein.

The system 900 can include one or more processors 915, a memory 930, an electronic apparatus 965, and a communications unit 935. The memory 930 can be structured to include a database. The processor(s) 915, the memory 930, and the communications unit 935 can be arranged to operate as a processing unit to control operation of the measuring device 907 and to perform operations on the signals collected by the measuring device 907 to determine whether the measuring device 907 in a borehole is in casing or the measuring device 907 is out of casing, in a manner similar or identical to the procedures discussed herein. A data processing unit 920, structured to conduct a plurality of test analsyses, can be implemented as a single unit or distributed among the components of the system 900 including electronic apparatus 965. The processor(s) 915 and the memory 930 can operate to control activation of the measuring device 907 and to manage processing schemes in accordance with measurement procedures and signal processing in a manner similar or identical to the procedures discussed herein. The data processing unit 920 and other components of the system 900 can be configured, for example, to operate similar to or identical to the components discussed herein or similar to or identical to methods discussed herein.

The communications unit 935 can include downhole communications for appropriately located measuring devices in a drilling operation. Such downhole communications can include a telemetry system. The communications unit 935 may use combinations of wired communication technologies and wireless technologies at frequencies that do not interfere with on-going measurements.

The system 900 can also include a bus 27, where the bus 27 provides electrical conductivity among the components of the system 900. The bus 27 can include an address bus, a data bus, and a control bus, each independently configured or in an integrated format. The bus 27 can be realized using a number of different communication mediums that allows for the distribution of components of the system 900. Use of the bus 27 can be regulated by the processor(s) 915. Bus 927 can be realized as a communication network. Such a communication network may use a number of different transmission media.

In various embodiments, the peripheral devices 945 can include additional storage memory and other control devices that may operate in conjunction with the processor(s) 915 and the memory 930. In an embodiment, the processor(s) 915 can be realized as a processor or a group of processors that may operate independently depending on an assigned function.

The system 900 can include display unit(s) 955 as a distributed component on the surface at a drilling operation, which can be used with instructions stored in the memory 930 to implement a user interface 962 to monitor the operation of the measuring device 907 or components distributed within the system 900. The user interface 962 may be used to input parameter values for thresholds such that the system 900 can operate autonomously substantially without user intervention. The user interface 962 can also provide for manual override and change of control of the system 900 to a user. Such a user interface 962 can be operated in conjunction with the communications unit 935 and the bus 27.

Figure 10:
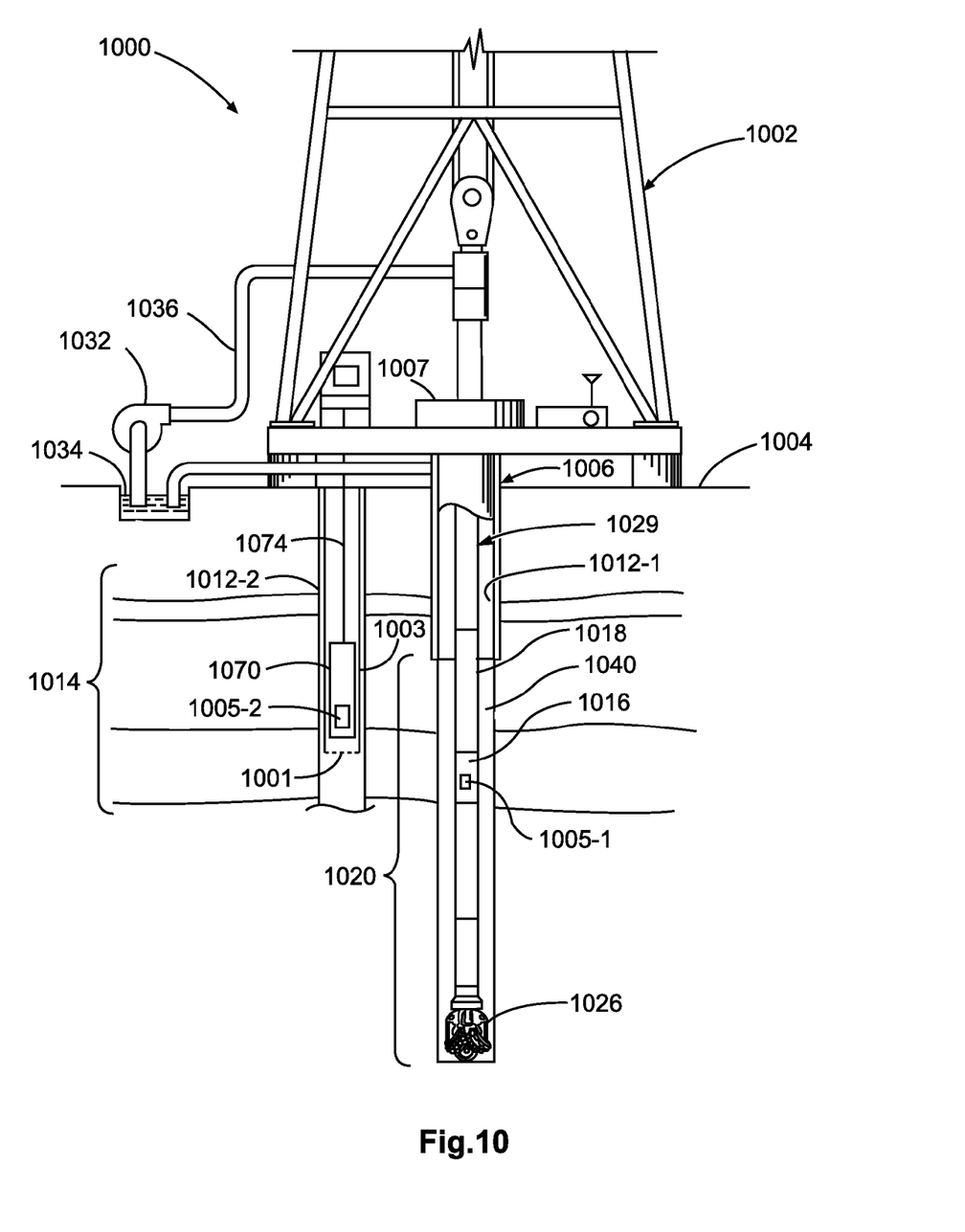
FIG. 10 depicts an example system at a drilling site, the system being operable to evaluate whether a measuring device operable in a borehole is in casing or the measuring device is out of casing, in accordance with various embodiments.

FIG. 10 depicts an example embodiment of a system 1000 at a drilling site, where the system includes instrumentality to manage measurement tools 1005-1 and 1005-2. The management of these tools can include determining whether a measuring device of the measurement tools 1005-1 and 1005-2 is in casing or out of casing as taught herein. The measurement tools 1005-1 and 1005-2 can be realized in a similar or identical manner to arrangements taught herein to perform testing to evaluate properties of regions downhole and to conduct testing related to the disposition of these measuring tools. The system can be constructed to conduct a plurality of test analyses on data collected, where the plurality of test analyses are structured to determine the in/out status of measuring devices of the measurement tools 1005-1 and 1005-2. The measurement tool 1005-2 may be implemented in a wireline arrangement in which a determination can be made as to whether the measuring device of measurement tool 1005-2 extends beyond an end 1001 of a casing 1003. The measurement tool 1005-1 may be implemented in a MWD arrangement in which a determination can be made as to whether the measuring device of measurement tool 1005-1 extends out from a housing of the measurement tool 1005-1 or a drill collar 1016 on or in which the measurement tool 1005-1 is mounted. In this instance, the housing and the drill collar 1016 are casings with respect to the measurement tool 1005-1. Components of the measurement tools 1005-1 and 1005-2 made be integrated downhole with the measuring device or distributed in the system 1000 including having surface components. The system 1000 can include a drilling rig 1002 located at a surface 1004 of a well 1006 and a string of drill pipes, that is, a drill string 1029, connected together so as to form a drilling string that is lowered through a rotary table 1007 into a wellbore or borehole 1012-1. The drilling rig 1002 can provide support for the drill string 1029. The drill string 1029 can operate to penetrate the rotary table 1007 for drilling the borehole 1012-1 through subsurface formations 1014. The drill string 1029 can include the drill pipe 1018 and a bottom hole assembly 1020 located at the lower portion of the drill pipe 1018.

The bottom hole assembly 1020 can include the drill collar 1016 and a drill bit 1026. The drill bit 1026 can operate to create the borehole 1012-1 by penetrating the surface 1004 and the subsurface formations 1014. The bottom hole assembly 1020 can include the measurement tool 1005-1 attached to the drill collar 1016 to perform testing to evaluate properties of regions downhole and to conduct testing related to the disposition of measuring devices of the measurement tool 1005-1. The measurement tool 1005-1 can be structured for an implementation in a MWD system such as a logging-while-drilling LWD system. The housing containing tool the measurement tool 1005-1 can include electronics to activate generation of signals from measuring devices of the measurement tool 1005-1 into a formation being analyzed and collect responses from measuring devices of the measurement tool 1005-1. Such electronics can include a processing unit to provide analysis including a determination of the in/out status of measuring devices of the measurement tool 1005-1 to the surface over a standard communication mechanism for operating in a well. Alternatively, electronics can include a communications interface to provide signals output by the measurement tool 1005-1 to the surface over a standard communication mechanism for operating in a well, where these output signals can be analyzed at a processing unit at the surface including a determination of the in/out status of measuring devices of the measurement tool 1005-1.

During drilling operations, the drill string 1029 can be rotated by the rotary table 1007. In addition to, or alternatively, the bottom hole assembly 1020 can also be rotated by a motor (e.g., a mud motor) that is located downhole. The drill collars 1016 can be used to add weight to the drill bit 1026. The drill collars 1016 also can stiffen the bottom hole assembly 1020 to allow the bottom hole assembly 1020 to transfer the added weight to the drill bit 1026, and in turn, assist the drill bit 1026 in penetrating the surface 1004 and the subsurface formations 1014.

During drilling operations, a mud pump 1032 can pump drilling fluid (sometimes known by those of skill in the art as "drilling mud") from a mud pit 1034 through a hose 1036 into the drill pipe 1018 and down to the drill bit 1026. The drilling fluid can flow out from the drill bit 1026 and be returned to the surface 1004 through an annular area 1040 between the drill pipe 1018 and the sides of the borehole 1012-1. The drilling fluid may then be returned to the mud pit 1034, where such fluid is filtered. In some embodiments, the drilling fluid can be used to cool the drill bit 1026, as well as to provide lubrication for the drill bit 1026 during drilling operations. Additionally, the drilling fluid may be used to remove subsurface formation cuttings created by operating the drill bit 1026.

In various embodiments, the measurement tool 1005-2 may be included in a tool body 1070 coupled to a logging cable 1074 such as, for example, for wireline applications. The tool body 1070 containing the measurement tool 1005-2 can include electronics to activate generation of signals from measuring devices of the measurement tool 1005-2 into a formation being analyzed and collect responses from measuring devices of the measurement tool 1005-2. Such electronics can include a processing unit to provide analysis including a determination of the in/out status of measuring devices of the measurement tool 1005-2 to the surface over a standard communication mechanism for operating in a well. Alternatively, electronics can include a communications interface to provide signals output by the measurement tool 1005-2 to the surface over a standard communication mechanism for operating in a well, where these output signals can be analyzed at a processing unit at the surface including a determination of the in/out status of measuring devices of the measurement tool 1005-2. The logging cable 1074 may be realized as a wireline (multiple power and communication lines), a mono-cable (a single conductor), and/or a slick-line (no conductors for power or communications), or other appropriate structure for use in the borehole 1012-2. Though FIG. 10 depicts both an arrangement for wireline applications and an arrangement for LWD applications, the system 1000 may be also realized for one of the two applications.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
    collecting data from operating a measuring device in a borehole, the measuring device being a nuclear magnetic resonance device;
    conducting a plurality of test analyses on the data to determine whether the measuring device is in casing or out of casing, each test analysis of the plurality of test analyses being based on a function of frequency; and
    controlling the measuring device based on results of the test analyses.

2. The method of claim 1, wherein conducting the plurality of test analyses includes conducting the plurality of test analyses in a sequential fashion.

3. The method of claim 1, wherein conducting one or more test analyses of the plurality of test analyses is conducted as a verification procedure, after the result of one test analysis of the plurality of test analyses is determinate as to whether the measuring device is in casing or out of casing.

4. The method of claim 1, wherein conducting the plurality of test analyses includes conducting a center frequency test of the measuring device, a zero crossing test of the measuring device, and/or a Q test of the measuring device.

5. The method of claim 4, wherein the zero crossing test is a determination of zero crossing of phase of a measured gain as a function of frequency.

6. The method of claim 4, wherein the zero crossing test is a determination of zero crossing of an imaginary part of a measured gain as a function of frequency.

7. The method of claim 1, wherein conducting the plurality of test analyses on the data can be triggered by an occurrence of an operational measuring event.

8. The method of claim 7, wherein the occurrence of the operational measuring event includes detection of an absence of a measurement value in an analysis system or detection of an absence of reception of a measurement signal.

9. The method of claim 8, wherein the occurrence of the operational measuring event includes detection that porosity of a formation being measured drops to zero or to within a selected range greater than zero.

10. The method of claim 1, wherein determining the measuring device to be out of casing includes the result of a test analysis of the plurality of test analyses having a measurement test quantity being lower than a calibration value of the test analysis by more than an associated error.

11. The method of claim 1, wherein determining the measuring device to be in casing includes the result of a test analysis of the plurality of test analyses having a measurement test quantity being greater than a calibration value of the test analysis by more than a known value.

12. The method of claim 11, wherein the known value is greater than the calibration value of the test analysis by more than an associated error.

13. The method of claim 1, wherein conducting the plurality of test analyses includes comparing a pre-determined value to an absolute value of a product of a frequency shift corresponding to a zero-crossing, a frequency shift corresponding to maximum gain amplitude frequency shift, and a resonant ratio for a quality factor.

14. The method of claim 1, wherein conducting the plurality of test analyses includes comparing a pre-determined value to absolute value of a product of a frequency shift corresponding to a zero-crossing, a frequency shift corresponding to maximum gain amplitude frequency shift, and a ratio between a calibrated value of a resonant circuit bandwidth and a measured value of a resonant circuit bandwidth.

15. A machine-readable storage device having instructions stored thereon, which, when performed by a machine, cause the machine to perform operations, the operations comprising actions to:
    collect data from operating a measuring device in a borehole, the measuring device being a nuclear magnetic resonance device;
    conduct a plurality of test analyses on the data to determine whether the measuring device is in casing or out of casing, each test analysis of the plurality of test analyses being based on a function of frequency; and
    control the measuring device based on results of the test analyses.

16. A system comprising:
    a measuring device to generate signals to probe an underground formation, the measuring device being a nuclear magnetic resonance device;
    a data processing unit structured to conduct a plurality of test analyses on data collected operating the measuring device, the plurality of test analyses structured to determine whether the measuring device is in casing or out of casing, each test analysis of the plurality of test analyses being based on a function of frequency; and
    a control unit to control the measuring device based on results of the test analyses.

17. The system of claim 16, wherein the data processing unit is operable to conduct the plurality of test analyses in a sequential fashion.

18. The system of claim 17, wherein the data processing unit is operable to conduct one or more test analyses of the plurality of test analyses to provide a verification procedure, after the result of one test analysis of the plurality of test analyses is determinate as to whether the measuring device is in casing or out of casing.

19. The system of claim 16, wherein the plurality of test analyses includes conducting a center frequency test of the measuring device, a zero crossing test of the measuring device, and a Q test of the measuring device.

20. The system of claim 19, wherein the zero crossing test is a determination of zero crossing of phase of a measured gain as a function of frequency.

21. The system of claim 19, wherein the zero crossing test is a determination of zero crossing of an imaginary part of a measured gain as a function of frequency.

22. The system of claim 16, wherein the control unit and the data processing unit are operable together to conduct the plurality of test analyses following a trigger generated in response to an occurrence of an operational measuring event.

23. The system of claim 22, wherein the occurrence of the operational measuring event includes detection of an absence of a measurement value in an analysis system or detection of an absence of reception of a measurement signal.

24. The system of claim 23, wherein the occurrence of the operational measuring event includes detection that porosity of a formation being measured drops close to zero.

25. The system of claim 16, wherein the data processing unit is operable to determine the measuring device to be out of casing from the result of a test analysis of the plurality of test analyses having a measurement test quantity being lower than a calibration value of the test analysis by more than an associated error.

26. The system of claim 16, wherein the data processing unit is operable to determine the measuring device to be in casing from the result of a test analysis of the plurality of test analyses having a measurement test quantity being greater than a calibration value of the test analysis by more than a known value.

27. The system of claim 26, wherein the known value is greater than the calibration value of the test analysis by more than an associated error.

28. The system of claim 16, wherein the data processing unit is operable to conduct the plurality of test analyses to include a comparison of a pre-determined value to an absolute value of a product of a frequency shift corresponding to a zero-crossing, a frequency shift corresponding to maximum gain amplitude frequency shift, and a resonant ratio for a quality factor.

29. The system of claim 16, wherein the data processing unit is operable to conduct the plurality of test analyses to include a comparison of a pre-determined value to absolute value of a product of a frequency shift corresponding to a zero-crossing, a frequency shift corresponding to maximum gain amplitude frequency shift, and a ratio between a calibrated value of a resonant circuit bandwidth and a measured value of a resonant circuit bandwidth.

* * * * *